US007731657B2

(12) United States Patent
Stafford (10) Patent No.: US 7,731,657 B2
(45) Date of Patent: Jun. 8, 2010

(54) ANALYTE SENSOR INTRODUCER AND METHODS OF USE

(75) Inventor: Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 85 days.

(21) Appl. No.: 11/216,932

(22) Filed: Aug. 30, 2005

(65) Prior Publication Data

US 2007/0060814 A1   Mar. 15, 2007

(51) Int. Cl.
*A61B 5/00* (2006.01)
*A61B 5/05* (2006.01)

(52) U.S. Cl. .................. 600/309; 600/345; 600/347; 600/365

(58) Field of Classification Search ........... 600/222, 600/223, 224, 225, 583, 309, 345–366, 347
See application file for complete search history.

(56) References Cited

U.S. PATENT DOCUMENTS

| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |
| 4,925,268 A | 5/1990 | Iyer et al. |

(Continued)

FOREIGN PATENT DOCUMENTS

EP   0098592   1/1984

(Continued)

OTHER PUBLICATIONS

Armour, J. C. et al., "Application of Chronic Intravascular Blood Glucose Sensor in Dogs", *Diabetes*, vol. 39 Dec. 1990 , 1519-1526.

(Continued)

*Primary Examiner*—Patricia C Mallari
(74) *Attorney, Agent, or Firm*—Jackson & Co., LLP (57) ABSTRACT

Method and apparatus for providing an introducer for transcutaneous placement of at least a portion of an analyte sensor through the skin of a patient is provided.

11 Claims, 5 Drawing Sheets

U.S. PATENT DOCUMENTS

| | | |
|---|---|---|
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,372,427 A | 12/1994 | Padovani et al. |
| 5,379,238 A | 1/1995 | Stark |
| 5,390,671 A * | 2/1995 | Lord et al. .................. 600/347 |
| 5,391,250 A | 2/1995 | Cheney, II et al. |
| 5,408,999 A | 4/1995 | Singh et al. |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A * | 12/1996 | Erickson et al. ............. 600/576 |
| 5,586,553 A * | 12/1996 | Halili et al. ................. 600/316 |
| 5,593,852 A | 1/1997 | Heller et al. |
| 5,628,310 A | 5/1997 | Rao et al. |
| 5,653,239 A | 8/1997 | Pompei et al. |
| 5,711,001 A | 1/1998 | Bussan et al. |
| 5,711,861 A | 1/1998 | Ward et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,088,608 A | 7/2000 | Schulman et al. |
| 6,091,976 A | 7/2000 | Pfeiffer et al. |
| 6,093,172 A | 7/2000 | Funderburk et al. |
| 6,119,028 A | 9/2000 | Schulman et al. |
| 6,120,676 A | 9/2000 | Heller et al. |
| 6,121,009 A | 9/2000 | Heller et al. |
| 6,122,351 A | 9/2000 | Schlueter, Jr. et al. |
| 6,134,461 A | 10/2000 | Say et al. |
| 6,162,611 A | 12/2000 | Heller et al. |
| 6,175,752 B1 * | 1/2001 | Say et al. .................... 600/345 |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,514,718 B2 | 2/2003 | Heller et al. |
| 6,551,494 B1 | 4/2003 | Heller et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 * | 10/2004 | Mann et al. ............ 340/870.28 |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,873,268 B2 | 3/2005 | Lebel et al. |
| 6,892,085 B2 * | 5/2005 | McIvor et al. ............... 600/347 |
| 6,931,327 B2 | 8/2005 | Goode, Jr. et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,997,907 B2 | 2/2006 | Safabash et al. |
| 6,998,247 B2 | 2/2006 | Monfre et al. |
| 7,003,341 B2 * | 2/2006 | Say et al. .................... 600/345 |
| 7,024,245 B2 | 4/2006 | Lebel et al. |
| 7,041,068 B2 * | 5/2006 | Freeman et al. ............. 600/583 |
| 7,052,483 B2 | 5/2006 | Wojcik |
| 7,056,302 B2 * | 6/2006 | Douglas .................... 604/136 |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |

| | | |
|---|---|---|
| 7,110,803 B2 | 9/2006 | Shults et al. |
| 7,113,821 B1 * | 9/2006 | Sun et al. ............... 604/21 |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,192,450 B2 | 3/2007 | Brauker et al. |
| 7,198,606 B2 * | 4/2007 | Boecker et al. ............ 600/583 |
| 7,226,978 B2 | 6/2007 | Tapsak et al. |
| 7,276,029 B2 | 10/2007 | Goode, Jr. et al. |
| 7,297,151 B2 * | 11/2007 | Boecker et al. ............ 606/181 |
| 7,666,149 B2 * | 2/2010 | Simons et al. ............. 600/583 |
| 2002/0019022 A1 | 2/2002 | Dunn et al. |
| 2002/0042090 A1 | 4/2002 | Heller et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0134347 A1 | 7/2003 | Heller et al. |
| 2003/0168338 A1 | 9/2003 | Gao et al. |
| 2003/0187338 A1 | 10/2003 | Say et al. |
| 2003/0212379 A1 | 11/2003 | Bylund et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0186362 A1 | 9/2004 | Brauker et al. |
| 2004/0199059 A1 | 10/2004 | Brauker et al. |
| 2004/0254433 A1 | 12/2004 | Bandis et al. |
| 2004/0267300 A1 | 12/2004 | Mace |
| 2005/0027177 A1 | 2/2005 | Shin et al. |
| 2005/0031689 A1 | 2/2005 | Shults et al. |
| 2005/0043598 A1 | 2/2005 | Goode et al. |
| 2005/0090607 A1 | 4/2005 | Tapsak et al. |
| 2005/0112169 A1 | 5/2005 | Brauker et al. |
| 2005/0131346 A1 | 6/2005 | Douglas |
| 2005/0176136 A1 | 8/2005 | Burd et al. |
| 2005/0187720 A1 | 8/2005 | Goode Jr. et al. |
| 2005/0192557 A1 | 9/2005 | Brauker et al. |
| 2005/0239154 A1 | 10/2005 | Feldman et al. |
| 2005/0245795 A1 | 11/2005 | Goode Jr. et al. |
| 2005/0245799 A1 | 11/2005 | Brauker et al. |
| 2006/0001538 A1 | 1/2006 | Kraft et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 * | 1/2006 | Brister et al. ............ 600/345 |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0222566 A1 | 10/2006 | Brauker et al. |
| 2007/0027381 A1 * | 2/2007 | Stafford ............... 600/347 |
| 2007/0078320 A1 * | 4/2007 | Stafford ............... 600/347 |
| 2007/0078321 A1 * | 4/2007 | Mazza et al. ............ 600/347 |
| 2007/0163880 A1 | 7/2007 | Woo et al. |
| 2007/0203966 A1 | 8/2007 | Brauker et al. |
| 2007/0235331 A1 | 10/2007 | Simpson et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-2004/061420 | 7/2004 |
| WO | WO-2005/089103 | 9/2005 |

OTHER PUBLICATIONS

Bennion, N. et al., "Alternate Site Glucose Testing: A Crossover Design", *Diabetes Technology & Therapeutics*, vol. 4, No. 1 2002, 25-33.

Blank, T. B. et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624 2002, 1-10.

Brooks, S. L. et al., "Development of an On-Line Glucose Sensor for Fermentation Monitoring", *Biosensors 3* 1987/88, 45-56.

Cass, A. et al., "Ferrocene-Medicated Enzyme Electrode for Amperometric Determination of Glucose", *Analytical Chemistry*, vol. 56, No. 4 Apr. 1984, 667-671.

Complaint, Amended, "*Abbott Diabetes Care, Inc. v. Dexcom Inc.*", Jun. 27, 2006.

Complaint, "*Abbott Diabetes Care, Inc. v. Dexcom, Inc.*", Aug. 11, 2005.

Csoregi, E. et al., "Design and Optimization of a Selective Subcutaneously Implantable Glucose Electrode Based on Wired' Glucose Oxidase", *Analytical Chemistry*, vol. 67 No. 7 Apr. 1, 1995, 1240-1244.

Feldman, B. et al., "A Continuous Glucose Sensor Based on Wired Enzyme Technology—Results from a 3-Day Trial in Patients with Type 1 Diabetes", *Diabetes Technology & Therapeutics*, vol. 5, No. 5 2003, 769-779.

Feldman, B. et al., "Correlation of Glucose Concentrations in Interstitial Fluid and Venous Blood During Periods of Rapid Glucose Change".

Johnson, P. C., "Peripheral Circulation", *John Wiley & Sons* 1978, 198.

Jungheim, K. et al., "How Rapid Does Glucose Concentration Change in Daily Life of Patients with Type 1 Diabetes?", , 250.

Jungheim, K. et al., "Risky Delay of Hypoglycemia Detection by Glucose Monitoring at the Arm", *Diabetes Care*, vol. 24 (7) Jul. 2001, 1303-1304.

Kaplan, S. M., "Wiley Electrical and Electronics Engineering Dictionary", *IEEE Press* 2004, 141, 142,548,549.

Lortz, J. et al., "What is Bluetooth? We Explain the Newest Short-Range Connectivity Technology", *Smart Computing Learning Series, Wireless Computing*, vol. 8 Issue 5 2002, 72-74.

Malin, S. F. et al., "Noninvasive Prediction of Glucose by Near-Infrared Diffuse Reflectance Spectroscopy", *Clinical Chemistry*, vol. 45, No. 9 1999, 1651-1658.

McGarraugh, G. et al., "Glucose Measurements Using Blood Extracted from the Forearm and the Finger", *TheraSense, Inc.*, Alameda, CA, 16 Pages.

McGarraugh, G. et al., "Physiological Influences on Off-Finger Glucose Testing", *Diabetes Technology & Therapeutics*, vol. 3, No. 3 2001, 367-376.

McKean, B. D. et al., "A Telemetry-Instrumentation System for Chronically Implanted Glucose and Oxygen Sensors", *IEEE Transactions on Biomedical Engineering*, vol. 35, No. 7 Jul. 1988, 526-532.

PCT, "International Search Report and Written Opinion of International Searching Authority", *PCT Application No. PCT/US2006/033885 filed* Aug. 29, 2006.

Pickup, J. C. et al., "Implantable Glucose Sensors: Choosing the Appropriate Sensing Strategy", *Biosensors 3* 1987-1988, 335-346.

Pickup, J. C. et al., "In Vivo Molecular Sensing in Diabetes Mellitus: An Implantable Glucose Sensor with Direct Electron Transfer", *Diabetologia, 32* 1989, 213-217.

Pishko, M. V. et al., "Amperometric Glucose Microelectrodes Prepared Through Immobilization of Glucose Oxidase in Redox Hydrogels", *Analytical Chemistry*, vol. 63, No. 20 Oct. 15, 1991, 2268-2272.

Quinn, C. P. et al., "Kinetics of Glucose Delivery to Subcutaneous Tissue in Rats Measured with 0.3-mm Amperometric Microsensors", *The American Physiological Society* 1995, E155-E161.

Roe, J. N. et al., "Bloodless Glucose Measurements", *Critical Review in Therapeutic Drug Carrier Systems*, vol. 15 Issue 3 1998, 199-241.

Sakakida, M. et al., "Development of Ferrocene-Mediated Needle-Type Glucose Sensor as a Measure of True Subcutaneous Tissue Glucose Concentrations", *Artif. Organs Today* vol. 2 No. 2 1992, 145-158.

Sakakida, M. et al., "Ferrocene-Mediated Needle-Type Glucose Sensor Covered with Newly Designed Biocompatible Membrane", *Sensors and Actuators B*, vol. 13-14 1993, 319-322.

Salehi, C. et al., "A Telemetry-Instrumentation System for Long-Term Implantable Glucose and Oxygen Sensors", *Analytical Letters, 29(13)* 1996, 2289-2308.

Schmidtke, D. W. et al., "Measurement and Modeling of the Transient Difference Between Blood and Subcutaneous Glucose Concentrations in the Rat After Injection of Insulin", *Proceedings of the National Academy of Sciences* vol. 95 1998, 294-299.

Shaw, G. W. et al., "In Vitro Testing of a Simply Constructed, Highly Stable Glucose Sensor Suitable for Implantation in Diabetic Patients", *Biosensors & Bioelectronics 6* 1991, 401-406.

Shichiri, M. et al., "Glycaemic Control in Pancreatectomized Dogs with a Wearable Artificial Endocrine Pancreas", *Diabetologia* vol. 24 1983, 179-184.

Shichiri, M. et al., "In Vivo Characteristics of Needle-Type Glucose Sensor—Measurements of Subcutaneous Glucose Concentrations in Human Volunteers", *Hormone and Metabolic Research Supplement Series* vol. 20 1988, 17-20.

Shichiri, M. et al., "Membrane Design for Extending the Long-Life of an Implantable Glucose Sensor", *Diab. Nutr. Metab.* vol. 2 1989, 309-313.

Shichiri, M. et al., "Needle-type Glucose Sensor for Wearable Artificial Endocrine Pancreas", *Implantable Sensors for Closed-Loop Prosthetic Systems, Chapter 15* Ko, Wen H (Ed), Futura Publishing Company, Inc. 1985, 197-210.

Shichiri, M. et al., "Telemetry Glucose Monitoring Device With Needle-Type Glucose Sensor: A Useful Tool for Blood Glucose Monitoring in Diabetic Individuals", *Diabetes Care*, vol. 9, No. 3 May-Jun. 1986, 298-301.

Shichiri, M. et al., "Wearable Artificial Endocrine Pancreas With Needle-Type Glucose Sensor", *The Lancet* Nov. 20, 1982, 1129-1131.

Shults, M. C. et al., "A Telemetry-Instrumentation System for Monitoring Multiple Subcutaneously Implanted Glucose Sensors", *IEEE Transactions on Biomedical Engineering*, vol. 41, No. 10 Oct. 1994, 937-942.

Sternberg, R. et al., "Study and Development of Multilayer Needle-Type Enzyme-Based Glucose Microsensors", *Biosensors 4* 1988, 27-40.

Thompson, M. et al., "In Vivo Probes: Problems and Perspectives", *Clinical Biochemistry*, vol. 19 Oct. 1986, 255-261.

Turner, A. et al., "Diabetes Mellitus: Biosensors for Research and Management", *Biosensors 1* 1985, 85-115.

U.S., "Patent Reexamination U.S. Appl. No. 90/007,903", Request for Reexamination of U.S. Patent No. 6,565,509 Jan. 25, 2006.

U.S., "Patent Reexamination U.S. Appl. No. 90/007,910", Request for Reexamination of U.S. Patent No. 6,175,752 Feb. 1, 2006.

U.S., "Patent Reexamination U.S. Appl. No. 90/007,913", Request for Reexamination of U.S. Patent No. 6,329,161 Feb. 1, 2006.

U.S., "Patent Reexamination U.S. Appl. No. 90/007,914", Request for Reexamination of U.S. Patent No. 6,329,161 Feb. 1, 2006.

U.S., "Patent Reexamination U.S. Appl. No. 90/008,172", Request for Reexamination of U.S. Patent No. 6,990,366 Aug. 16, 2006.

U.S., "Patent Reexamination U.S. Appl. No. 90/008,173", Request for Reexamination of U.S. Patent No. 6,134,461 Aug. 16, 2006.

U.S., "Patent Reexamination U.S. Appl. No. 90/008,457", Request for Reexamination of U.S. Patent No. 6,990,366 Jan. 23, 2007.

U.S., "Patent Reexamination U.S. Appl. No. 90/008,665", Request for Reexamination of U.S. Patent No. 6,284,478 May 25, 2007.

U.S., "Patent Reexamination U.S. Appl. No. 90/008,713", Request for Reexamination of U.S. Patent No. 6,329,161 Jul. 25, 2007.

Updike, S. J. et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4* 1997, 117-137.

Velho, G. et al., "Strategies for Calibrating a Subcutaneous Glucose Sensor", *Biomed. Biochim. Acta, 48* 1989, 957-964.

Wilson, G. S. et al., "Progress Toward the Development of an Implantable Sensor for Glucose", *Clinical Chemistry* vol. 38(9) 1992, 1613-1617.

International Preliminary Report on Patentability and Written Opinion of the International Searching Authority for PCT Application No. PCT/US2006/033885 filed Aug. 29, 2006 to Abbott Diabetes Care, Inc.

\* cited by examiner

ANALYTE SENSOR INTRODUCER AND METHODS OF USE

BACKGROUND

The present invention relates to data monitoring systems. More specifically, the present invention relates to method and apparatus for providing an analyte sensor introducer for transcutaneous placement of an analyte sensor into a patient for use in analyte monitoring systems including glucose monitoring systems.

Glucose monitoring systems generally include a sensor such as a subcutaneous analyte sensor for detecting analyte levels such as glucose levels, a transmitter (such as an RF transmitter) in communication with the sensor and configured to receive the sensor signals and to transmit them to a corresponding receiver unit by for example, using RF data transmission protocol. The receiver may be operatively coupled to a glucose monitor that performs glucose related calculations and data analysis such as for example, trend analysis, data management and medical treatment planning and management.

The transmitter may be mounted or adhered to the skin of a patient and also in signal communication with the sensor, At least a portion of which may be implanted into the skin of the patient. Generally, the sensor is configured to detect and measure the glucose levels of the patient over a predetermined period of time, and the transmitter is configured to transmit the measured glucose levels over the predetermined period of time for further analysis. To initially set up the sensor so that the sensor contacts and electrodes are in fluid contact with the patient's analyte fluids, it is important to properly insert the sensor wholly or partially through the patient's skin and securely retain the sensor during the time that the sensor is configured to detect analyte levels. In addition to accurate positioning of the sensor through the skin of the patient, it is important to minimize the level of pain associated with the insertion of the sensor through the patient's skin.

In view of the foregoing, it would be desirable to have a sensor introducing mechanism including sensor introducer for accurate and easy insertion of the sensor through the skin of a patient or otherwise to properly position the sensor, e.g., transcutaneously, so that the sensor maybe configured to detect analyte levels of the patient. Also, it would be desirable to have a method and apparatus to have a sensor introducing mechanism that places the sensor at least partially through the skin of the patient with ease and relative little pain.

SUMMARY OF THE INVENTION

In one embodiment, there is provided an analyte sensor introducer configuration and methods of use which provides reduced insertion/extraction force through the skin of the patient thereby reducing the trauma to the patient's skin. In this manner, in one embodiment, the puncture through the skin of the patient can be maintained relatively small, which in turn, results in less bleeding and bruises to the patient's skin, allowing for a faster healing time.

In a further embodiment of the present invention, the introducer is integrated into the housing of an analyte sensor inserter and a mounting unit of a sensor control unit, or a base housing which is configured to receive a data transmitter (or a transceiver). As such, a single device which incorporates the sensor insertion mechanism as well as providing the support structure for mounting the transmitter to a patient is provided. The data transmitter in one embodiment is configured for electrical communication with the sensor, where the sensor is configured to detect the patient's analyte level, and the transmitter configured to transmit (wirelessly or otherwise) to a monitoring unit such as a glucose monitor unit or an insulin pump.

In this manner, in accordance with the various embodiments of the present invention, the sensor may be introduced through the skin of the patient for accurate transcutaneous placement while lessening the pain to the patient during the sensor placement process.

DETAILED DESCRIPTION

Figures 1, 2:
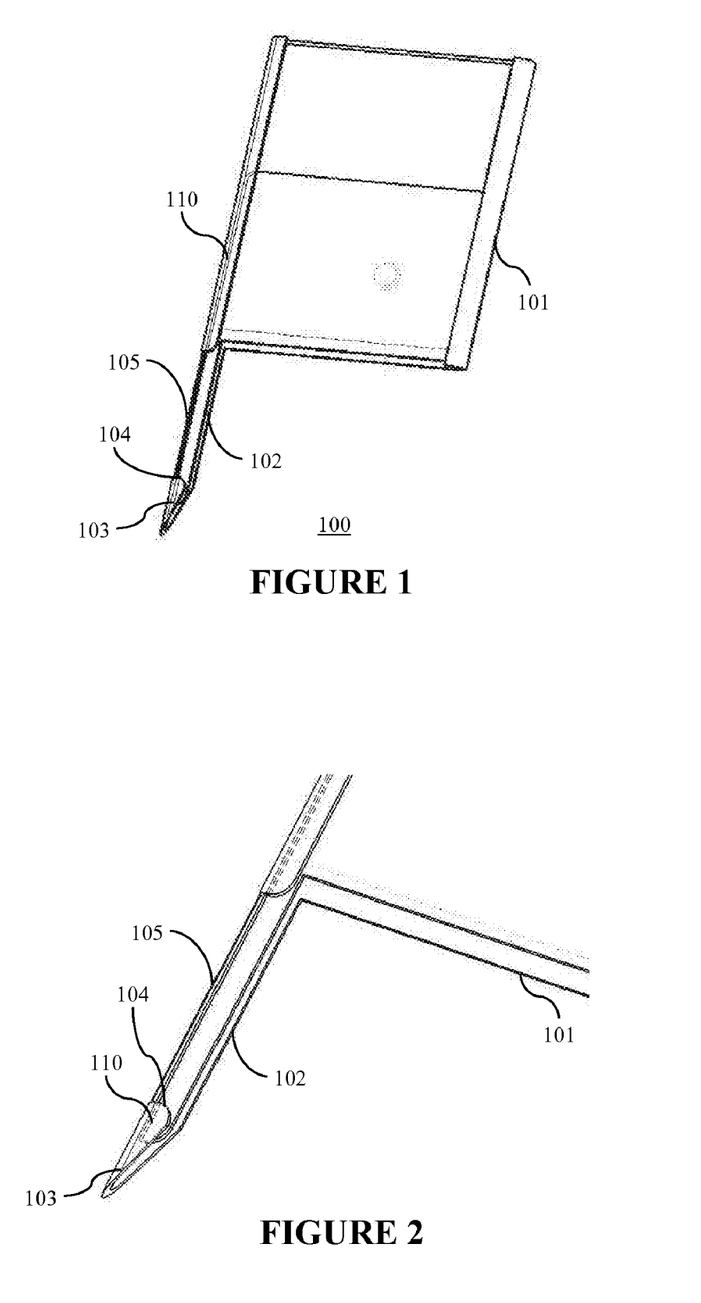
FIG. 1 illustrates a perspective view of an analyte sensor introducer in accordance with one embodiment of the present invention.
FIG. 2 is a detailed view of the shaft portion of the analyte sensor introducer shown in FIG. 1 in accordance with one embodiment of the present invention.

FIG. 1 illustrates a perspective view of an analyte sensor introducer in accordance with one embodiment of the present invention. Referring to the Figure, there is provided an introducer 100 having a body portion 101 and a shaft portion 105. The shaft portion 105 includes a substantially relatively sharp edge segment 103 which is configured to first contact the skin of the patient during the placement of the introducer through the patient's skin for transcutaneous placement of an analyte sensor 110. As shown, the sensor 110 is configured to be retained within the shaft portion 105 and held in position during the sensor 110 insertion process through the patient's skin by the substantially hollow cylindrical shape of the shaft portion 105 as shown in the Figure.

Referring to FIG. 1, the tip of the analyte sensor 110 is retained at the edge segment 103 of the introducer 100 during the placement of the sensor 110 transcutaneously through the patient's skin. It should be noted that the edge segment 103 of the introducer 100 is configured to first pierce through the patient's skin, and at substantially same time, guide the retained sensor 110 maintained in the shaft portion 105 of the introducer 100 through the pierced skin of the patient. When the sensor 110 is placed at the desired location under the skin, the introducer 100 is configured to be retracted from the patient, leaving the sensor 110 in place. More specifically, during the introducer removal process from the patient, a radial configuration 104 of the shaft portion 105 is configured to guide the removal of the introducer 100 from the pierced skin.

FIG. 2 shows a detailed view of the shaft portion of the analyte sensor introducer shown in FIG. 1 in accordance with one embodiment of the present invention. In further embodiments, the shaft portion 105 may have a ribbed configuration so as to provide additional strength during the insertion and retraction of the introducer through the skin of the patient. Moreover, as shown in FIGS. 1 and 2, the shaft portion 105 of the introducer 100 includes a substantially longitudinal slit opening 102 which is provided to allow the introducer 100 to be completely de-coupled from the sensor 110 retained within the shaft portion 105 during the placement thereof, so that the introducer 100 may be removed completely from the patient, while leaving in place the sensor 110.

In this manner, in one embodiment of the present invention, the introducer 100 may be configured to reduce the insertion and extraction forces through the patient's skin, thus reducing trauma to the skin. By maintaining a relatively small skin puncture, it is possible to reduce the amount of potential bleeding during the skin piercing process for transcutaneous sensor placement, and likewise result is less bruising and also faster healing.

As described above, in one embodiment of the present invention, the analyte sensor is positioned within the substantially hollow shaft portion 105 of the introducer 100 such that the edge segment 103 of the introducer 100 guides the sensor 110 into and through the skin puncture. In one embodiment, the edge segment 103 may be sharpened and polished to facilitate a smooth puncture and a clean cut through the patient's skin. Moreover, the radial configuration 104 of the shaft portion 105 as discussed above provides a transition when the introducer 100 exits the puncture so as to allow for a smooth and relatively painless removal of the introducer from the patient.

Figure 3:
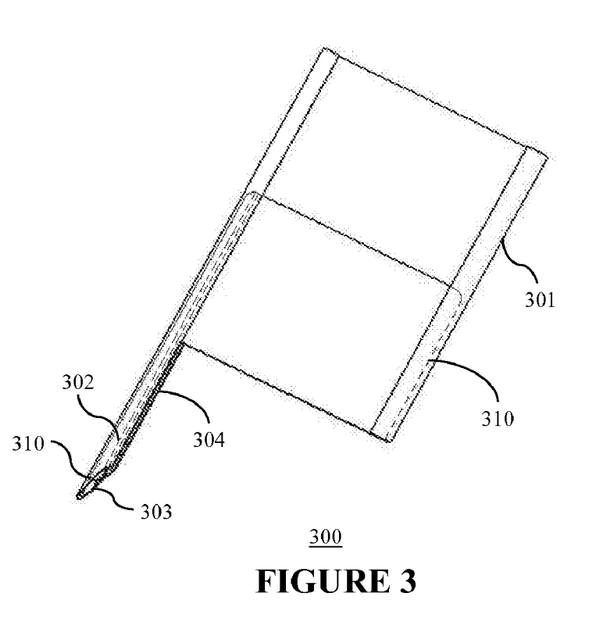
FIG. 3 illustrates a perspective view of an analyte sensor introducer in accordance with another embodiment of the present invention.
Figure 4:
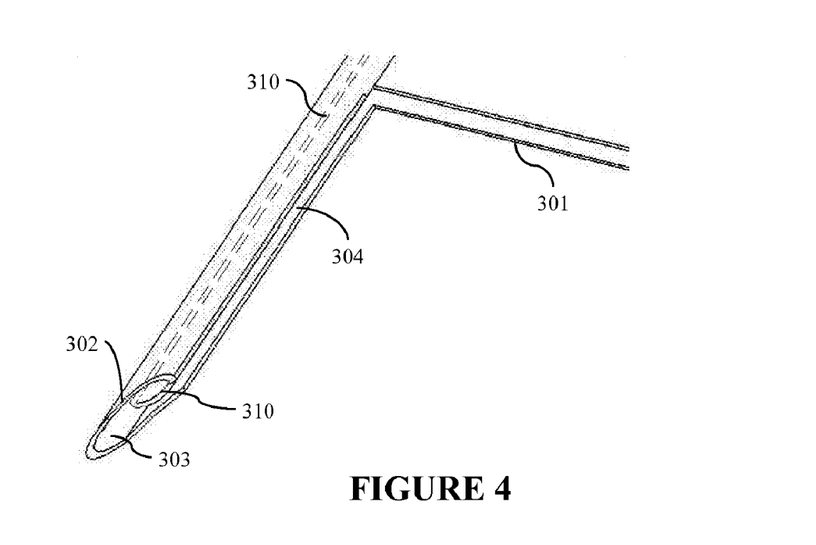
FIG. 4 is a detailed view of the shaft portion of the analyte sensor introducer shown in FIG. 3 in accordance with another embodiment of the present invention.

FIG. 3 illustrates a perspective view of an analyte sensor introducer in accordance with another embodiment of the present invention, and FIG. 4 is a detailed view of the shaft portion of the analyte sensor introducer shown in FIG. 3 in accordance with another embodiment of the present invention. Referring to FIGS. 3 and 4, introducer 300 includes a body portion 301 and a shaft portion 302, where the shaft portion 302 includes a relatively sharp and tapered edge segment 303 as shown. Also shown in the Figures is a longitudinal opening 304 along the shaft portion 302 of the introducer 300 extending from the edge segment 303.

In this manner, in one embodiment of the present invention, the analyte sensor 310 is placed along the hollow shaft portion 302 of the introducer 300 such that the shaft portion of the sensor 310 is guided by the edge segment 303 of the introducer 300 during the transcutaneous placement of the sensor 310. Accordingly, the edge segment 303 is configured to first pierce the patient's skin and thereafter the sensor 310 retained within the shaft portion 302 of the introducer 300 is introduced through the patient's skin following the directional movement of the introducer 300.

As described above, the introducer in one embodiment may be configured to substantially retain the sensor 310 and place the sensor through the skin of the patient so that the sensor 310 is easily and quickly guided through the skin, minimizing the potential for the sensor 310 to deflect off (and thus not penetrate) the skin during the insertion process. This is particularly guided in one embodiment by the edge segment 303 of the introducer 300 as shown in the Figures above. Additionally, the longitudinal slit opening 304 substantially parallel to the length of the shaft portion 302 of the introducer 300 is provided to allow the introducer 300 to be removed completely from the patient while leaving the sensor 310 in place after deploying the same under the skin.

Moreover, in accordance with the various embodiments, and as substantially shown in the Figures described above, the introducer configuration is provided such that the amount of drag and frictions during the introducer introduction through the patient's skin is reduced, while the substantially hollow and cylindrical shaft portion of the introducer is configured to minimize the necessary force to deploy the introducer so that the sensor is properly placed through the patient's skin, while the speed of the insertion and removal of the introducer is also optimized for minimizing pain and skin trauma.

Figure 5:
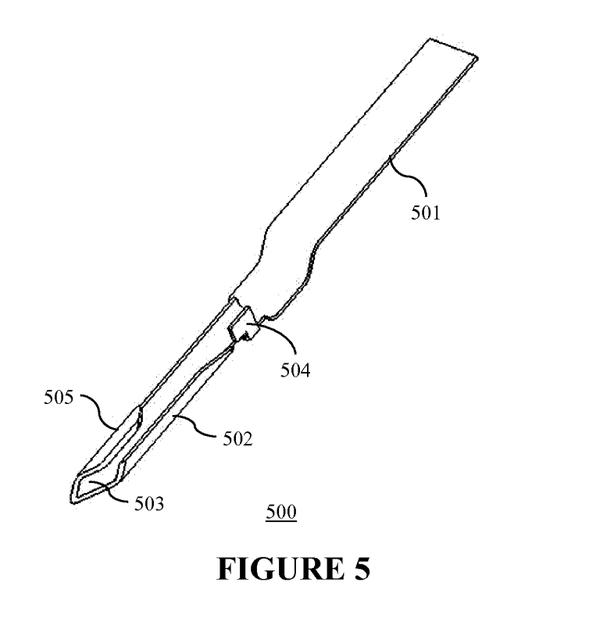
FIG. 5 illustrates a perspective view of an analyte sensor introducer in accordance with a further embodiment of the present invention.
Figure 6:
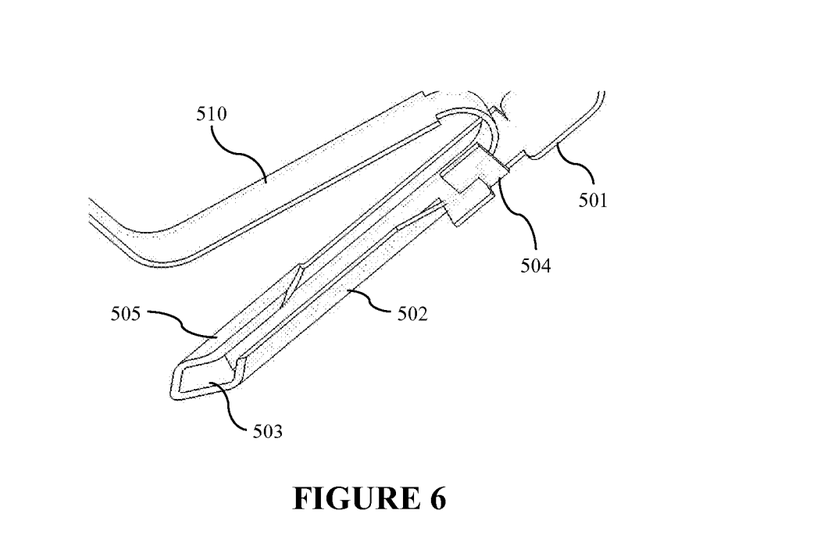
FIG. 6 is a detailed view of the shaft portion of the analyte sensor introducer shown in FIG. 5 in accordance with a further embodiment of the present invention.

FIG. 5 illustrates a perspective view of an analyte sensor introducer in accordance with a further embodiment of the present invention, while FIG. 6 shows a detailed view of the shaft portion of the analyte sensor introducer shown in FIG. 5 in accordance with a further embodiment of the present invention. Referring to the Figures, introducer 500 includes a body portion 501 and a shaft portion 502, where the shaft portion 502 further includes a substantially sharp edge segment 503, an upper fold segment 505 and a tab segment 504. In one embodiment, the upper fold segment 505 is configured to substantially retain the sensor 510 within the shaft portion 502 of the introducer 500, while the tab segment 504 is similarly configured to retain the sensor 510 within the shaft portion 502 so as to guide or maintain the position of the sensor during the insertion of the introducer 500 through the patient's skin.

More specifically, the shaft portion 502 is configured so as to substantially retain the portion of the sensor 510 that is to be placed under the skin of the patient so as to be in fluid contact with the patient's analyte. Moreover, the edge segment 503 of the introducer 500 includes a substantially sharp and angled tip for piercing the patient's skin. Indeed, the edge segment 503 of the introducer 500 is sharp and tapered to facilitate skin piercing while minimizing skin trauma. In this manner, it is possible to minimize the size of the skin wound at the piercing site where the introducer 500 is placed through the skin, and thus, the patient will likely experience a faster healing time.

Referring back to FIGS. 5 and 6, it can be seen also that the shaft portion 502 is configured so that the sensor 510 that is retained substantially within the shaft portion 502 during the insertion of the introducer 500 through the skin, can be completely de-coupled and separated from the sensor 510 when the sensor 510 is placed in its final position. In this manner, the introducer 500 may be removed from the patient, while at least a portion of the sensor is retained in fluid contact with the patient's analyte so as to monitor its levels, for example.

Figure 7:
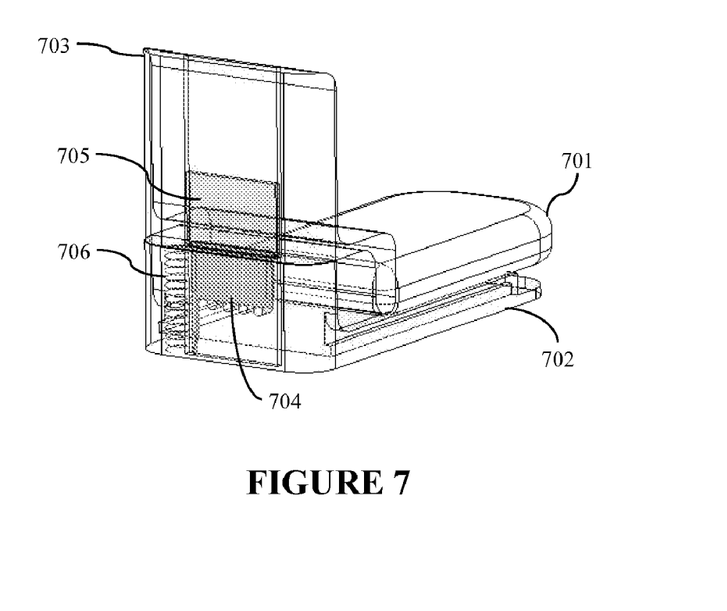
FIG. 7 illustrates an analyte sensor introducer integrated with the transmitter mount housing with a drive mechanism for placement on the skin of a patient in accordance with yet another embodiment of the present invention.

FIG. 7 illustrates an analyte sensor introducer integrated with the transmitter mount housing with a drive mechanism for placement on the skin of a patient in accordance with yet another embodiment of the present invention. Referring to the Figure, there is provided a transmitter mount 702 configured to receive or mount with a transmitter 701. The transmitter mount 702 in one embodiment is configured to couple with a drive mechanism 703 that may be optionally be reusable. The transmitter mount 702 housing may be further configured to integrate a spring 706 which, in conjunction with the drive mechanism 703, is configured to provide insertion and/retraction force for introducing the sensor 704 and the sensor introducer 705. Referring back to FIG. 7, the transmitter mount 702 in one embodiment also includes a sensor 704 and a sensor introducer 705 integrated within the housing of the transmitter mount 702.

In operation, the patient in one embodiment arms (or cocks) the drive mechanism 703 to generate the sufficient inertial force needed to drive the introducer 705 and the sensor 704 through the patient's skin. More specifically, in one embodiment, the introducer 705 and the sensor 704 are provided in a fully assembled package within the transmitter mount 702. Thus, when the patient wishes to place the sensor 704 subcutaneously, the drive mechanism 703 is armed and the patient places the transmitter mount 702 on the surface of the patient's skin where the patient wishes to place the sensor 704. Thereafter, the driver mechanism 703 is operated to drive the introducer 705 and the sensor 704 through the skin of the patient.

In one embodiment, the drive mechanism may include spring biased mechanism, magnetic force implementation, as well as a motor and gear combination, or the like, so as to provide the necessary force for inserting the introducer 705 and the sensor 704, as well as to retract the introducer 705. Furthermore, within the scope of the present invention, the drive mechanism 703 may be activated by using one or more of an activation button, a lever, plunger, a switch, a knob or any type of suitable activation mechanism that the patient may easily operate to activate the drive mechanism 703.

Figure 8:
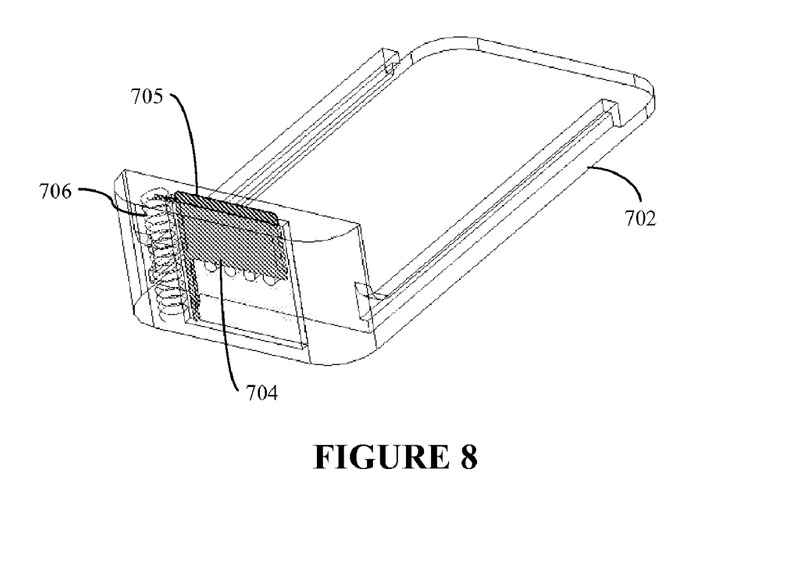
FIG. 8 illustrates the introducer integrated with the transmitter mount housing of FIG. 7 in pre-deployment position in accordance with yet another embodiment of the present invention.
Figure 9:
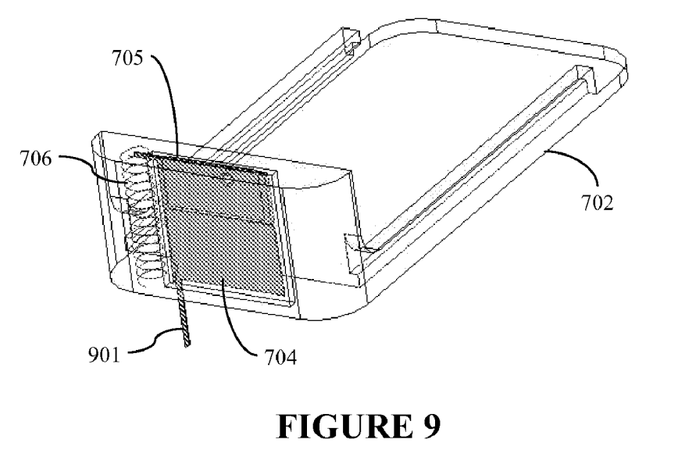
FIG. 9 illustrates the introducer integrated with the transmitter mount housing of FIG. 7 after sensor deployment position in accordance with yet another embodiment of the present invention.

Referring back to the Figures, FIGS. 8 and 9 illustrate the introducer integrated with the transmitter mount housing of FIG. 7 in pre-deployment and post deployment positions, respectively, in accordance with yet another embodiment of the present invention. Indeed, as shown in FIG. 9, after the sensor has been deployed and inserted into the skin of the patient, the tip portion 901 of the sensor 704 is positioned out of the housing of the transmitter mount 702 so as to be transcutaneously placed under the skin of the patient.

In this manner, in one embodiment of the present invention, the sensor 704 may be substantially precisely guided through the transmitter mount 702 and positioned at a specified depth under the patient's skin, e.g., in the subcutaneous tissue. When the insertion is completed, the spring 706 as shown in the Figures in one embodiment is configured to retract the introducer 705 out of the patient, so as to be retained within the transmitter mount 702. Thereafter, the drive mechanism 703 may be removed from the transmitter mount 702 and may be reused for future sensor insertion with one or more other sensors. Once the drive mechanism is removed, the transmitter 701 is placed in position and coupled with the transmitter mount 702 so as to establish electrical connection with the appropriate electrodes of the sensor 704 in order to begin transmission of the detected analyte levels to a receiving device such as a receiver/monitoring unit.

In the manner described above, in accordance with one embodiment of the present invention, such "on-board" insertion configuration of analyte sensors eliminates the need for a sensor delivery unit (such as a separate insertion device), and thereby reducing the associated material costs, weight, packaging, handling, as well as disposal thereof. Additionally, the number of steps that are necessary for the patient to perform to introduce and position the analyte sensor is reduced which provides significant advantages, especially in continuous monitoring systems where the sensor typically requires replacement at a predetermined interval.

Moreover, in certain embodiments, the transmitter 701 may be integrated into the transmitter mount 702 so as to provide a unitary piece of construction. Such embodiments reduce the number of separate components and reduce the number of steps a user performs by omitting or minimizing the steps of attaching or mounting a transmitter to the base portion. Additional detailed information on the detection, monitoring and analysis of analyte levels are described in further detail in U.S. Pat. No. 6,175,752 entitled "Analyte Monitoring Device and Methods of Use" the disclosure of which is incorporated herein by reference for all purposes.

In the manner described above, in accordance with one embodiment of the present invention, there is provided an introducer, comprising a body portion, and a shaft portion extending substantially from an edge of the body portion, the shaft portion including a tapered end, the shaft portion configured to substantially retain a sensor, and further, where the tapered end is configured to guide the sensor through a skin layer.

In one embodiment, the shaft portion may be substantially hollow, and further, the shaft portion may include an opening substantially along the length of the shaft portion.

Additionally, the opening of the shaft portion may be configured to be wider than the width of the sensor such that the sensor may be displaced out of the shaft portion through the opening.

Further, the shaft portion may be configured to retain at least a portion of the sensor substantially subcutaneously when the shaft portion is removed from the skin layer.

In a further embodiment, the tapered end of the shaft portion may be configured to pierce the skin layer, and further, wherein at least a portion of the sensor is substantially retained within the shaft portion while the tapered end is piercing through the skin layer.

Moreover, when the tapered end of the shaft portion is transcutaneously introduced to the skin layer, the sensor may be substantially contemporaneously transcutaneously introduced through the skin layer.

In one aspect, the sensor may include an analyte sensor, where the analyte sensor includes a glucose sensor. In a further aspect of the present invention, the sensor may include other types of sensors including, but not limited to short term or long term analyte sensors, blood glucose sensors, implanted electrochemical sensors, or the like.

Also, the analyte sensor may be in fluid contact with the patient's analyte.

A method of introducing a sensor in a further embodiment of the present invention includes aligning a tapered end of an introducer substantially onto a sensor insertion site of a patient, piercing the skin at the sensor insertion site of the patient with the tapered end of the introducer, guiding a sensor with the introducer through the skin, and removing the introducer substantially completely from the patient while subcutaneously retaining at least a portion of the sensor in the patient.

In one embodiment, the guiding step may include the step of substantially entirely retaining at least a portion of the sensor within a shaft portion of the introducer.

Moreover, the tapered end of the introducer may include a substantially sharp edge segment configured to pierce the skin, where the sharp edge segment of the tapered end may be substantially configured at an angle greater than 45 degrees relative to the direction of the sharp edge segment piercing the skin.

An introducer in a further embodiment of the present invention includes a body portion, and a shaft portion extending substantially from an edge of the body portion, the shaft portion including a tapered end, the shaft portion configured to substantially retain an analyte sensor, and further, where the tapered end may be configured to guide the analyte sensor through a skin layer such that at least a portion of the analyte sensor is in fluid contact with an analyte of a patient under the skin layer.

An analyte monitoring system in a further embodiment of the present invention includes a sensor, an introducer, and a transmitter, the introducer including a body portion, and a shaft portion extending substantially from an edge of the body portion, the shaft portion including a tapered end, the shaft portion configured to substantially retain the sensor, and further, where the tapered end is configured to guide the sensor through a skin layer, and the transmitter configured to operatively coupled to the sensor to transmit a data associated with a detected analyte level received from the sensor.

In a further embodiment, the system may also include a receiver operatively coupled to the transmitter, the receiver configured to receive the data from the transmitter. Moreover, the transmitter in one embodiment may be configured to wirelessly transmit the data.

An inserter kit in accordance to still a further embodiment of the present invention includes a sensor, an introducer that includes a body portion, a shaft portion, and a drive mechanism, the shaft portion extending substantially from an edge of the body portion, the shaft portion including a tapered end, the shaft portion configured to substantially retain the sensor, and further, wherein the tapered end is configured to guide the sensor through a skin layer of a patient, and the drive mechanism coupled to the body portion, the drive mechanism configured to drive at least a section of the shaft portion through the skin layer, and further, to retract the at least the section of the shaft portion substantially completely out of the patient, where at least a portion of the sensor is placed subcutaneously when the at least the section of the shaft portion of the introducer is retracted from the skin layer such that the sensor is substantially in fluid contact with the analyte of the patient.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An integrated transmitter mount, comprising:
   a housing for placement on a skin layer;
   an introducer disposed within the housing and including a body portion, and a shaft portion extending substantially from an edge of the body portion, the shaft portion including a tapered end and an upper fold segment, the shaft portion retaining a sensor, and further, the tapered end guiding the sensor through the skin layer during sensor insertion and the upper fold segment limiting the movement of the sensor when the sensor is guided through the skin layer, the introducer retained within the housing after retraction from the skin layer and sensor insertion through the skin layer; and
   a drive mechanism detachably coupled to the housing to provide insertion force to the introducer during sensor insertion, the drive mechanism detached from the housing after the sensor is guided through the skin layer and the introducer is positioned within the housing.

2. The mount of claim 1 wherein the shaft portion is substantially hollow.

3. The mount of claim 1 wherein the shaft portion includes an opening substantially along the length of the shaft portion.

4. The mount of claim 3 wherein the opening is configured to be wider than the width of a sensor retained therein such that the sensor may be displaced out of the shaft portion through the opening.

5. The mount of claim 3 wherein the shaft portion is configured to retain at least a portion of the sensor substantially subcutaneously when the shaft portion is removed from the skin layer.

6. The mount of claim 1 wherein the tapered end of the shaft portion is configured to pierce the skin layer, and further, wherein at least a portion of the sensor is substantially retained within the shaft portion while the tapered end is piercing through the skin layer.

7. The mount of claim 1 wherein when the tapered end of the shaft portion is transcutaneously introduced to the skin layer, the sensor is substantially contemporaneously transcutaneously introduced through the skin layer.

8. The mount of claim 1 wherein the sensor includes an analyte sensor.

9. The mount of claim 8 wherein the analyte sensor is a glucose sensor.

10. The mount of claim 8 wherein the introducer is configured to position the analyte sensor in fluid contact with a patient's analyte.

11. An inserter kit, comprising:
    a transmitter mount housing;
    a sensor provided within the housing;
    an introducer coupled to the sensor and provided within the housing, the introducer including:
       a body portion; and
       a shaft portion extending substantially from an edge of the body portion, the shaft portion including a tapered end and an upper fold segment, the shaft portion retaining the sensor, and the tapered end guiding the sensor through a skin layer of a patient, the upper fold segment limiting the movement of the sensor when the sensor is guided through the skin layer, the body portion and the shaft portion retained within the transmitter mount housing after sensor positioning;
    a drive mechanism detachably coupled to the housing to drive at least a section of the shaft portion through the skin layer, the drive mechanism retracting the at least the section of the shaft portion of the introducer out of the patient, the drive mechanism detached from the housing after the introducer is retained within the housing;
    wherein at least a portion of the sensor is placed subcutaneously when the at least the section of the shaft portion of the introducer is retracted from the skin layer such that the sensor is substantially in fluid contact with an analyte of the patient.

* * * * *